United States Patent [19]

Mayland

[11] Patent Number: 4,904,295
[45] Date of Patent: Feb. 27, 1990

[54] SELECTIVE WEED CONTROL IN CEREAL GRAIN CROPS

[75] Inventor: Paul G. Mayland, Fargo, N. Dak.

[73] Assignee: Hoechst Roussel Pharmaceuticals, Inc., Somerville, N.J.

[21] Appl. No.: 207,975

[22] Filed: Jun. 15, 1988

[51] Int. Cl.$^4$ ............................................. A01N 43/52
[52] U.S. Cl. ......................................................... 71/88
[58] Field of Search ............................................. 71/88

[56] References Cited

U.S. PATENT DOCUMENTS 4,668,276  5/1987  Handte et al. .......................... 71/88

Primary Examiner—Richard L. Raymond
Attorney, Agent, or Firm—Tatsuya Ikeda

[57] ABSTRACT

A method of selectively controlling weeds such as wild oats and foxtail in certain cereal grain crops, such as wheat and barley, is described which comprises applying an effective amount of a composition comprising as effective components suitable proportions of Fenoxaprop-ethyl (namely, (±)ethyl 2-8 4-[(6-chloro-2-benozoxazoly)oxy]phenyl]propanoate),2,4-D(namely, 2,4-dichlorophenoxyacetic acid) and Bromoxynil(-namely, 3,5-dibromo-4-hydroxybenzonitrile) or MCPA (namely, 4-chloro-2-methylphenoxyacetic acid). The composition affords an excellent balance between suppression of the phytotoxicity of Fenoxaprop-ethyl and preservation of the herbicidal activity of Fenoxaprop-ethyl, thus accomplishing a selective weed control in certain cereal grain crops.

30 Claims, No Drawings

SELECTIVE WEED CONTROL IN CEREAL GRAIN CROPS

The present invention relates to a method of selectively controlling weeds in cereal grains. More specifically, it relates to a method of selectively controlling weeds such as wild oat and foxtail in certain cereal grain crops, particularly wheat and barley, with minimal adverse effect upon the growth of cereal grain crops, which method comprises applying an effective amount of a composition comprising as effective components suitable proportions of (a) Fenoxaprop-ethyl (namely, (±)ethyl 2-[4-[(6-chloro-2-benzoxazolyl)oxy]phenoxy]-propanoate which has a structure depicted by Formula 1 below), 2,4-D (namely, 2,4-dichlorophenoxyacetic acid which has a structure depicted by Formula 2 below) and Bromoxynil (namely, 3,5-dibromo-4-hydroxybenzonitrile which has a structure depicted by Formula 3 below) or (b) Fenoxaprop-ethyl, 2,4-D and MCPA (namely, 4-chloro-2-methylphenoxyacetic acid) which has a structure depicted by Formula 4 below) or (c) Fenoxaprop-ethyl, 2,4-D, Bromoxynil and MCPA.

The present invention is also directed to novel compositions described above which are useful for the selective control of weeds in cereal grain crops when applied in a suitable amount.

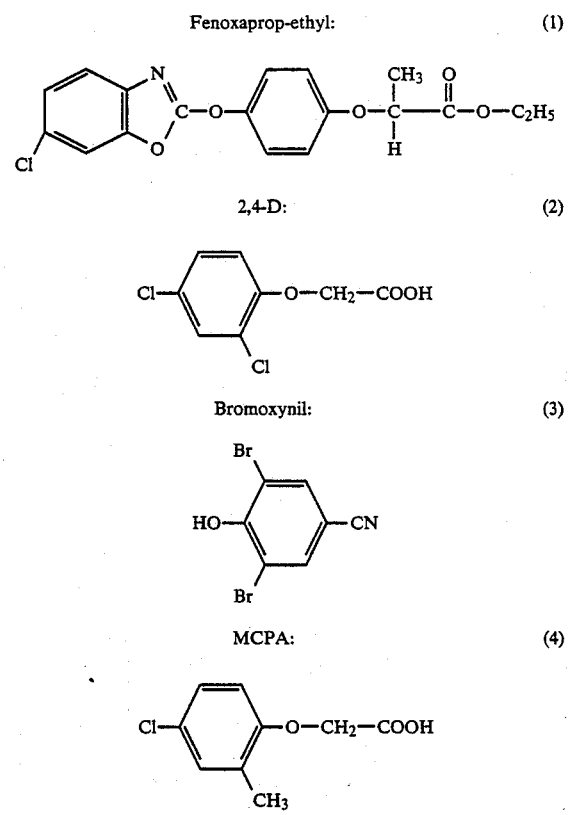

Handte et al., U.S. Pat. No. 4,668,276 discloses the use of certain aryloxy compounds as antidotes (safeners) for plant treatment agents such as herbicides. Included in the disclosure of said patent is the use of a compound of the formula, Ar—O—A—Z, wherein Ar is a phenyl group mono- or di-substituted by halogen atoms or $(C_1-C_4)$-alkyl; A is —$CH_2$— or —$CH(CH_3)$—; and Z is —COOR', R' being hydrogen, $(C_1-C_{12})$-alkyl or a cation of an organic or inorganic base, as a safener for protecting wheat against the phytotoxic side effects of Fenoxaprop-ethyl. Said safener compounds of the formula Ar—O—A—Z include 2,4-D and MCPA. However, said patent does not disclose or suggest the three-way combination of Fenoxaprop-ethyl, 2,4-D and MCPA or Bromoxynil according to this invention which affords a particularly desirable balance between supression of the phytotoxicity of Fenoxaprop-ethyl and preservation of the herbicidal activity of Fenoxaprop-ethyl.

As indicated above, Fenoxaprop-ethyl, while effective as a herbicide, usually has an adverse effect known as phytotoxicity upon crop plants such as cereal grain plants. Thus, in order to obtain a maximum yield of desired crop from a given acreage of soil, it is very desirable to have an optimal balance between the suppression of the phytotoxic effect of Fenoxaprop-ethyl and preservation of the herbicidal effect of Fenoxaprop-ethyl. The present invention is based on my discovery that when compositions (a) Fenoxaprop-ethyl+2,4-D+Bromoxynil or (b) Fenoxaprop-ethyl+2,4-D+MCPA or (c) Fenoxaprop-ethyl+2,4-D+Bromoxynil+MCPA, in which the components have suitable proportions, are used in a suitable amount for growing cereal grain crops such as wheat and barley, various weeds such as wild oats, foxtail, lambsquarter, wild mustard and redroot pigweed are controlled well without any substantial adverse effect (phytotoxic effect) upon the desired crops. The desirable balance between the herbicidal effect and phytotoxic effect of Fenoxaprop-ethyl is obtained by virtue of the presence of 2,4-D+Bromoxynil, or 2,4-D+MCPA, or 2,4-D+Bromoxynil+MCPA used in combination with Fenoxaprop-ethyl. For the sake of convenience, Fenoxaprop-ethyl will be referred to as component I, 2,4-D as component II and Bromoxynil or MCPA or Bromoxynil+MCPA as component III. Component I can be considered as a herbicide and components II and III as antidotes. The balance mentioned above afforded by this invention is substantially better than those afforded by prior art combinations such as Fenoxaprop-ethyl+2,4-D, Fenoxaprop-ethyl+MCPA, Fenoxaprop-ethyl+Bromoxynil or Fenoxaprop-ethyl+MCPA+Bromoxynil as can be seen from the experimental data presented below.

Suitable proportions of components I, II and III in the composition according to this invention vary depending upon the nature of crop plant and weed to be treated and to a small extent upon the identity of component III, and they can be determined on a case-by-case basis by appropriate tests. Usually, however, the proportions are within the range of I:II:III=1.0:0-.2-5.0:0.3-5.0 by weight, and preferably within the range of I:II:III=1.0:0.5-3.0:1.0-4.0.

As to component II (2,4-D), it may be used in this invention not only as a free acid form, but also in the form of a salt formed with a loweralkylamine or diloweralkylamine, particularly, dimethylamine, or in the form of an ester formed with a loweralkanol such as butanol or octanol, the term "lower" signifying 1 to 8 carbon atoms. Thus, the term "2,4-D" as used in the specification and the appended claims shall mean 2,4-dichlorophenoxyacetic acid, its salt with a loweralkylamine or diloweralkylamine or its ester with a loweralkanol, the term "lower" signifying 1 to 8 carbon atoms.

The components I, II and III may be applied to plants either separately or simultaneously, but it is usually preferable to apply them simultaneously as a premixed composition. The term "composition" as used in this specification and the appended claims shall encompass situations where the components I, II and III are applied to plants separately at different points in time.

The "composition" of this invention is usually applied to plants or parts of plants after emergence.

There is no particular limitation as to the form or formulation in which the individual components or the composition is used. Suitable forms and formulations are well known in the art.

Suitable amount of the composition applied in the field is, in terms of the amount of component I, usually about 50–500 g/hectare, preferably about 80–400 g/hectare.

As mentioned earlier, crop plants for which this invention can be used advantageously are cereal grains particularly wheat and barley, and weeds which are controlled effectively by this invention include wild oats, foxtail, lambsquarter, wild mustard and redroot pigweed.

The present invention will be described below with reference to examples, but they should not be interpreted as limiting the scope of this invention.

EXAMPLE 1

Fenoxaprop-ethyl and various compositions comprising fenoxaprop-ethyl, 2,4-D, bromoxynil and/or MCPA were tested on the field as to their efficacies for controlling weeds and their phytotoxicities on spring wheat, barley and durum. Tame oat was used as a representation of weeds. Tame oat, spring wheat, barley and durum were grown in a large number of plots. Some of the plots had all four of the above plants growing thereon, whereas some other plots had only one or two kinds of plants growing thereon as a substantial population. Weed control (% injury to the weed) and phytotoxicity to each crop plant (% injury to crop plant) were evaluated based on visual observation of the plants after the treatment with chemicals. For the sake of reference, certain plots were left untreated with chemicals. Said visual observation was conducted about two weeks after the application of chemicals which had taken place when the plants generally had one or two tillers. In making the numerical evaluation for any given plant, only those plots which had a sufficient population of the plant thereon were chosen. A phytotoxicity of below 20% is generally considered acceptable in the art. The results of the tests are summarized in Table 1, where fenoxaprop-ethyl is designated as component A, 2,4-D (in the form of dimethylamine salt) as component B, Bromoxynil as component C and MCPA as component D. The same designations are also used in Tables 2 and 3.

TABLE 1

| Treatment | Amounts (gram per hectare) | Weed Contol (% of injury) Tame Oat | Phytotoxicity (% of injury) | | |
|---|---|---|---|---|---|
| | | | Wheat | Barley | Durum |
| Untreated | | 0 | 0 | 0 | 0 |
| A | 180 | 100 | 7 | 82 | 83 |
| | 200 | 100 | 15 | 88 | 88 |
| | 220 | 100 | 17 | 88 | 90 |
| | 240 | 100 | 13 | 85 | 87 |

TABLE 1-continued

| Treatment | Amounts (gram per hectare) | Weed Contol (% of injury) Tame Oat | Phytotoxicity (% of injury) | | |
|---|---|---|---|---|---|
| | | | Wheat | Barley | Durum |
| A + B | 180/200 | 100 | 0 | 17 | 45 |
| | 180/320 | 100 | 0 | 13 | 22 |
| | 220/200 | 99 | 0 | 15 | 50 |
| | 220/320 | 100 | 0 | 15 | 30 |
| A + D | 180/340 | 100 | 0 | 53 | 92 |
| | 180/460 | 100 | 2 | 45 | 88 |
| | 220/340 | 100 | 2 | 37 | 87 |
| | 220/460 | 100 | 3 | 58 | 92 |
| A + B + C | 180/200/140 | 100 | 0 | 17 | 32 |
| | 180/320/140 | 100 | 0 | 12 | 8 |
| | 220/200/140 | 100 | 0 | 17 | 27 |
| | 220/320/140 | 100 | 0 | 12 | 15 |
| A + B + D | 180/280/280 | 100 | 0 | 8 | 2 |
| | 240/280/280 | 100 | 0 | 12 | 8 |
| A + C + D | 180/140/340 | 100 | 0 | 70 | 90 |
| | 180/140/460 | 100 | 0 | 65 | 88 |
| | 220/140/340 | 100 | 7 | 68 | 92 |
| | 220/140/460 | 100 | 12 | 67 | 93 |

EXAMPLE 2

Fenoxaprop-ethyl (component A), 2,4-D (component B, in the form of dimethylamine salt) and Bromoxynil (component C) were combined at various proportions and tests were conducted in substantially the same manner as in Example 1. The results are summarized in Table 2.

TABLE 2

| Treatment | Amounts (gram per hectare) | Weed Contol (% of injury) Tame Oat | Phytotoxicity (% of injury) | | |
|---|---|---|---|---|---|
| | | | Wheat | Barley | Durum |
| Untreated | | 0 | 0 | 0 | 0 |
| A + B + C | 180/200/140 | 55 | 7 | 13 | 15 |
| | 180/200/280 | 58 | 8 | 17 | 20 |
| | 200/200/280 | 60 | 8 | 16 | 19 |
| | 220/200/140 | 62 | 8 | 17 | 13 |
| | 220/200/280 | 53 | 6 | 19 | 22 |
| | 240/200/280 | 58 | 9 | 28 | 26 |
| | 180/240/280 | 62 | 7 | 13 | 17 |
| | 200/240/280 | 60 | 9 | 19 | 21 |
| | 220/240/280 | 58 | 8 | 21 | 23 |
| | 240/240/280 | 62 | 8 | 20 | 24 |
| | 180/280/280 | 60 | 7 | 14 | 10 |
| | 200/280/280 | 57 | 9 | 17 | 17 |
| | 220/280/280 | 58 | 7 | 19 | 18 |
| | 240/280/280 | 62 | 8 | 19 | 20 |
| | 180/320/140 | 57 | 6 | 10 | 8 |
| | 180/320/280 | 60 | 6 | 12 | 9 |
| | 200/320/280 | 57 | 6 | 14 | 12 |
| | 220/320/140 | 62 | 6 | 15 | 9 |
| | 220/320/280 | 58 | 6 | 16 | 16 |
| | 240/320/280 | 58 | 8 | 26 | 18 |

EXAMPLE 3

Hard red spring wheat was used as an example of crop plant, and wild oat, lambsquarter, wild mustard and redroot pigweed were used as examples of weed, and tests were conducted in substantially the same manner as in Example 1. The results are summarized in Table 3.

TABLE 3

| Treatment | Amounts (gram per hectare) | Weed Contol (% of injury) | | | Phytotoxicity (% of injury) | |
|---|---|---|---|---|---|---|
| | | Wild Oats | Lambs-quarter | Wild Mustard | Redroot Pigweed | Wheat |
| Untreated | | 0 | 0 | 0 | 0 | 0 |
| A + B | 112/560 | 12 | 98 | 98 | 92 | 0 |
| | 224/560 | 23 | 97 | 95 | 90 | 0 |
| A + C | 112/280 | 52 | 73 | 83 | 52 | 15 |
| | 224/280 | 70 | 95 | 95 | 75 | 40 |
| A + D | 112/426 | 53 | 100 | 100 | 45 | 10 |
| | 224/426 | 67 | 93 | 94 | 70 | 25 |
| A + B + C | 112/280/280 | 42 | 100 | 100 | 87 | 0 |
| | 224/280/280 | 70 | 97 | 100 | 82 | 0 |

What is claimed:

1. A method of protecting a cereal grain crop plant from a weed which comprises applying to the plants or their environment a composition comprising effective herbicidal and anti-phytotoxic amounts of Fenoxaprop-ethyl, 2,4-D and MCPA, where the proportions of the components based on weights are within the range of Fenoxaprop-ethyl:2,4-D:MCPA=1.0:0.2-5.0:0.3-5.0.

2. A method of protecting a cereal grain crop plant from a weed which comprises applying to the plants or their environment a composition comprising effective herbicidal and anti-phytotoxic amounts of Fenoxaprop-ethyl, 2,4-D and Bromoxynil, where the proportions of the components based on weights are within the range of Fenoxaprop-ethyl:2,4-D:Bromoxynil=1.0:0.2-5.0:0.3-5.0.

3. A method of protecting a cereal grain crop plant from a weed which comprises applying to the plants or their environment a composition comprising effective herbicidal and anti-phytotoxic amounts of Fenoxaprop-ethyl, 2,4-D, MCPA and Bromoxynil, where the proportions of the components based on weights are within the range of Fenoxaprop-ethyl:2,4-D:(MCPA+Bromoxynil)=1.0:0.2-5.0:0.3-5.0.

4. The method as defined in claim 1, where the crop plant is wheat or barley.

5. The method as defined in claim 2, where the crop plant is wheat or barley.

6. The method as defined in claim 3, where the crop plant is wheat or barley.

7. The method as defined in claim 1, where the weed is wild oats or foxtail.

8. The method as defined in claim 2, where the weed is wild oats or foxtail.

9. The method as defined in claim 3, where the weed is wild oats or foxtail.

10. The method as defined in claim 4, where the weed is wild oats or foxtail.

11. The method as defined in claim 5, where the weed is wild oats or foxtail.

12. The method as defined in claim 6, where the weed is wild oats or foxtail.

13. The method as defined in claim 1, where the amount of composition applied is within the range of 50-500 g/hectare.

14. The method as defined in claim 2, where the amount of composition applied is within the range of 50-500 g/hectare.

15. The method as defined in claim 3, where the amount of composition applied is within the range of 50-500 g/hectare.

16. The method as defined in claim 1, where the proporations of the components based on weights are within the range of Fenoxaprop-ethyl:2,4-D:MCPA=1.0:0.5-3.0:1.0-4.0.

17. The method as defined in claim 2, where the proportions of the components based on weights are within the range of Fenoxaprop-ethyl:2,4-D:Bromoxynil=1.0:0.5-3.0:1.0-4.0.

18. The method as defined in claim 3, where the proportions of the components based on weights are within the range of Fenoxaprop-ethyl:2,4-D:(MCPA+Bromoxynil)=1.0:0.5-3.0:1.0-4.0.

19. The method as defined in claim 13, where the crop plant is wheat or barley.

20. The method as defined in claim 14, where the crop plant is wheat or barley.

21. The method as defined in claim 15, where the crop plant is wheat or barley.

22. The method as defined in claim 16, where the crop plant is wheat or barley.

23. The method as defined in claim 17, where the crop plant is wheat or barley.

24. The method as defined in claim 18, where the crop plant is wheat or barley.

25. A herbicidal and anti-phytotoxic composition comprising effective herbicidal and anti-phytotoxic amounts of Fenoxaprop-ethyl, 2,4-D and MCPA, where the proportions of the components based on weights are within the range of Fenoxaprop-ethyl:2,4-D:MCPA=1.0:0.2-5.0:0.3-5.0.

26. A herbicidal and anti-phytotoxic composition comprising effective herbicidal and anti-phytotoxic amounts of Fenoxaprop-ethyl, 2,4-D and Bromoxynil, where the proportions of the components based on weights are within the range of Fenoxaprop-ethyl:2,4-D:Bromoxynil=1.0:0.2-5.0:0.3-5.0.

27. A herbicidal and anti-phytotoxic composition comprising effective herbicidal and anti-phytotoxic amounts of Fenoxaprop-ethyl, 2,4-D, MCPA and Bromoxynil, where the proportions of the components based on weights are within the range of Fenoxaprop-ethyl:2,4-D:(MCPA+Bromoxynil)=1.0:0.2-5.0:0.3-5.0.

28. The composition as defined in claim 25, where the proportions of the components based on weights are within the range of Fenoxaprop-ethyl:2,4-D:MCPA=1.0:0.5-3.0:1.0-4.0.

29. The composition as defined in claim 26, where the proportions of the components based on weights are within the range of Fenoxaprop-ethyl:2,4-D:Bromoxynil=1.0:0.5-3.0:1.0-4.0.

30. The composition as defined in claim 27, where the proportions of the components based on weights are within the range of Fenoxaprop-ethyl:2,4-D:(MCPA+Bromoxynil)=1.0:0.5-3.0:1.0-4.0.

* * * * *